United States Patent [19]

Rheinish et al.

[11] Patent Number: 5,275,604
[45] Date of Patent: Jan. 4, 1994

[54] CONTOURED DUCT APPARATUS AND METHOD FOR INSERTION OF FLEXIBLE INTRAOCULAR LENS

[75] Inventors: Robert S. Rheinish, Huntington Beach; Allan R. Tonks, Fontana; Thomas P. Richards, Los Angeles, all of Calif.

[73] Assignee: Kabi Pharmacia Ophthalmics, Inc., Monrovia, Calif.

[21] Appl. No.: 985,026

[22] Filed: Dec. 3, 1992

[51] Int. Cl.$^5$ ............................................. A61F 9/00
[52] U.S. Cl. ......................................... 606/107; 623/6
[58] Field of Search ........................ 606/107; 623/4, 6

[56] References Cited

U.S. PATENT DOCUMENTS

| | | | |
|---|---|---|---|
| 3,150,406 | 9/1964 | Obitts | 606/107 |
| 4,214,585 | 7/1980 | Bailey, Jr. | 606/107 |
| 4,702,244 | 10/1987 | Mazzocco | 623/6 |
| 4,747,404 | 5/1988 | Jampel et al. | 623/6 |
| 4,834,094 | 5/1989 | Patton et al. | 128/303 R |
| 4,836,201 | 6/1989 | Patton et al. | 128/303 R |
| 4,862,885 | 9/1989 | Cumming | 128/303 R |
| 4,919,130 | 4/1990 | Stoy et al. | 606/107 |
| 4,934,363 | 6/1990 | Smith et al. | 606/107 |
| 5,066,297 | 11/1991 | Cumming | 606/107 |
| 5,123,905 | 6/1992 | Kelman | 606/107 |
| 5,190,552 | 3/1993 | Kelman | 606/107 |

OTHER PUBLICATIONS

"Consultation Section" edited by Samuel Masket, M.D., published in J Cataract Refract Surg-vol. 18, Mar. 1992, pp. 206-214.

Primary Examiner—Stephen C. Pellegrino
Assistant Examiner—Tamara L. Graysay
Attorney, Agent, or Firm—Poms, Smith, Lande & Rose

[57] ABSTRACT

An apparatus and associated method for deforming and inserting a flexible intraocular lens into an eye which permits the size of an ocular incision to be significantly smaller than the diameter of the intraocular lens being implanted, and its embodiments are suitable for use with lenses having radial flange or projecting filament haptics. The apparatus includes a contoured duct with a pair of internal guiding grooves configured to engage peripheral edges of the lens, curling the lens as it is advanced along the longitudinal duct axis from the elongated inlet to the coaxially aligned generally circular outlet of the duct. The guiding grooves are mutually opposed and converge along the length of the duct to essentially the periphery of the duct outlet. A lens is implanted utilizing this apparatus by loading the lens into a receiving chamber adjacent to the lens-curling contoured duct, inserting the outlet or a cannular probe communicating coaxially with said outlet into the ocular incision, and advancing the lens through the duct and then through the outlet into the eye.

20 Claims, 2 Drawing Sheets

CONTOURED DUCT APPARATUS AND METHOD FOR INSERTION OF FLEXIBLE INTRAOCULAR LENS

FIELD OF THE INVENTION

The present invention generally relates to apparatus and associated methods for implanting intraocular lenses, and more particularly, to simplified surgical instruments and methods for inserting a flexible intraocular lens through a small ocular incision.

BACKGROUND OF THE INVENTION

The eye of a human or animal is subject to the irreversible malfunctioning that occurs, for example, when the lens of the eye experiences permanent lens clouding, also known as a cataract condition. A well known surgical procedure for restoring vision impaired by lens clouding or other such aberration involves removal of the natural lens and replacement thereof with an artificial intraocular lens, commonly referred to as an IOL.

Early IOL's utilized lenses made of rigid material and having diameters ranging from six millimeters to eight millimeters, necessitating a commensurately large ocular incision for emplacement. More recent developments in IOL technology have made available flexible artificial lenses which are capable of being deformed by bending, squeezing or rolling to achieve a smaller size prior to insertion. This deformation of the lens prior to insertion allows the size of the associated incision to be significantly reduced to a length on the order of three millimeters. As a result of such shortening of the ocular incision, surgical trauma to the eye and the associated problems of post-operative astigmatism and prolonged healing time are substantially lessened.

For some years flexible lenses have been deformed by hand, utilizing forceps to fold or bend the lenses prior to insertion in the eye. To minimize the risk of scratching of the lenses as well as to reduce the physical difficulty inherent in such manual deformation techniques, a number of lens inserting devices have been developed. Among these is the apparatus disclosed in U.S. Pat. No. 4,834,09 (Patton) which utilizes a retractable sleeve to deform a flexible lens holder. Alternative devices are disclosed by U.S. Pat. No. 4,862,363 (Cummings), wherein the lens is collapsed between the two jaws of a holder, and in U.S. Pat. No. 4,934,363 (Smith), wherein an external paddle folds the lens as the flexible paddle is retracted into a rigid tube.

While each of these devices avoids some of the problems attendant to lens manipulation with forceps, each carries with it its own drawbacks. For example, the invention of U.S. Pat. No. 4,934,363 employs an elaborate and expensive drive mechanism to advance the lens through the holder; the invention of U.S. Pat. No. 4,862,885 utilizes complex ratchet and pawl operation to deform the lens; and the invention of U.S. Pat. No. 4,934,363 requires a membrane to be inserted into the eye along with the lens and then withdrawn from the eye, a process that not only introduces an extraneous object into the delicate surgical site, but adds a step the surgeon must perform to retrieve the membrane after lens implantation.

Additionally, these conventional insertion methods and devices carry the further drawbacks of potentially scratching the central light-focusing portion, or optic, of the lens, and of damaging the delicate lens haptics or fixation members. Haptics, which hold the optic in place after the lens is inserted into the eye, typically take the form of a radial flange that surrounds the lens optic, or of generally radially projecting filaments of various configurations (J-shaped or C-shaped, for example) extending in pairs from near the periphery of the optic. If a haptic is damaged during lens insertion, the incision may have to be enlarged to permit removal of the damaged lens, thus negating the advantages of the smaller initial incision.

Surgeons who have used existing lens insertion devices have expressed (see e.g., J. Cataract Refract Surg., March 1992, P.206) that a preferred instrument would provide (1) reliable and safe release of the IOL into the eye, (2) minimal incision enlargement, and (3) ease of loading the IOL into the instrument. Also mentioned frequently as a desirable goal is freedom from damage to the lens optic and haptics. Further, some previous insertion devices have been designed to manipulate only the radial flange configuration of intraocular lenses: an apparatus that operates well with both configurations, preparing both flange and loop haptic lenses for insertion with negligible distortion to the lens optic, would be desirable.

Accordingly, it is an object of this invention to provide a simplified, easy to operate device which combines in one instrument the functions of preparing a flexible intraocular lens for insertion through a small incision and of inserting the lens into the eye, eliminating the need for pre-folding or manipulating the lens outside the device.

A further object of the present invention is to provide a simple and inexpensive method of quickly and sequentially curling and inserting an intraocular lens through a small incision so that manual handling of the lens is minimized and permanent deformation of the lens is avoided.

A still further object is to provide an instrument that will safely accommodate and implant flexible intraocular lenses with both flange and loop haptic members.

SUMMARY OF THE INVENTION

These and other objects are achieved by the present invention which provides a surgical apparatus and associated method for quickly, easily and reliably deforming a foldable intraocular lens and sequentially inserting it through a significantly smaller ocular incision than would be otherwise necessary with the lens in its original undeformed shape.

An exemplary embodiment of the present invention includes a tubular body enclosing a uniquely contoured lens-curling duct with a transversely elongated inlet and internal surfaces configured to engage opposing peripheral edges of a flexible intraocular lens and to curl the lens as the lens is advanced along the longitudinal axis of the duct from the transversely elongated inlet to the generally circular duct outlet.

In operation, an unfolded intraocular lens is simply positioned initially adjacent to the inlet of the duct, in a plane defined by the transverse major axis of the inlet aperture. The inlet aperture of the lens curling duct is dimensioned to receive the undeformed diameter of the intraocular lens within the aperture's major axis, with the minor axis of the aperture dimensioned to provide sufficient clearance on either side of the initial plane of the lens to accommodate the depth of the lens. Each end of the inlet aperture major axis defines the curved, lens receiving proximal end of one of a pair of opposing longitudinally extending lens-engaging and guiding grooves. These mutually opposed grooves converge along the length of the duct from the duct inlet to the duct outlet to a point that is generally at the periphery of the circular outlet aperture. The point of convergence is above the initial lens plane that is defined by the intersecting of the inlet transverse major axis with the longitudinal axis of the duct.

As the lens is advanced longitudinally through the duct from the inlet to the outlet, the opposing peripheral edge portions of the lens are engaged by the longitudinal guiding grooves which serve to guide the lens edges toward each other with minimal radial pressure as the lens is advanced. Accordingly, curling of the lens is accomplished by the channeling of the peripheral lens edge portions in the guiding grooves up and toward one another rather than by radially compressing the lens.

Preferably, a plunger is used to advance the lens through the lens-curling duct. A central bore of the duct is of sufficient sectional area to allow the plunger to pass without restriction along the longitudinal axis of the duct for impelling the lens through the duct and out from the outlet. The plunger may be provided with a relief in its lens-engaging tip adjacent the lens to accommodate a trailing haptic of the lens, preventing damage to the haptic structure associated with the lens. The outlet of the apparatus is disposed to be positioned within the ocular incision, effecting implantation of the lens as the plunger releases it into the eye after the lens has been simultaneously deformed and advanced through the duct.

The procedure for utilizing the features of the present invention is efficient and uncomplicated. To implant a flexible intraocular lens through a surgical incision smaller than the undeformed diameter of the lens, a surgeon simply loads the lens through a loading door into the lens receiving chamber of the present invention. If the lens has extending loop haptics, a trailing haptic is positioned in the protective relief provided in the plunger's lens-engaging tip.

The lens is positioned within the inlet aperture of the lens-curling duct, a diameter of the lens extending from one side of the inlet major axis to its opposing side. The lens-receiving chamber aperture is closed off by shutting its releasable closure or door, and the instrument is then brought to the patient's eye so that the outlet of the duct is placed into the incision, which has been reduced in length as previously described.

When the outlet of the duct is positioned within the appropriate intraocular region, the plunger is brought into contact with the lens, first advancing the lens through the duct so that the grooves guiding the sides of the lens act to bring the lens edges substantially together, and then inserting the ultimately curled lens through the duct outlet into its designated place of implantation. The instrument is then withdrawn from the eye, the lens having been implanted through an incision on the order of one-half the diameter of the unflexed lens, successfully avoiding the necessity of retrieving from within the eye any membrane portion of an instrument.

Further objects and advantages of the contoured duct lens curling and insertion apparatus of the present invention, as well as a better understanding thereof, will be afforded to those skilled in the art from a consideration of the following detailed explanation of an exemplary embodiment thereof. Reference will be made to the appended sheets of drawings which will now be first described briefly.

DETAILED DESCRIPTION OF EXEMPLARY EMBODIMENT

Figure 1:
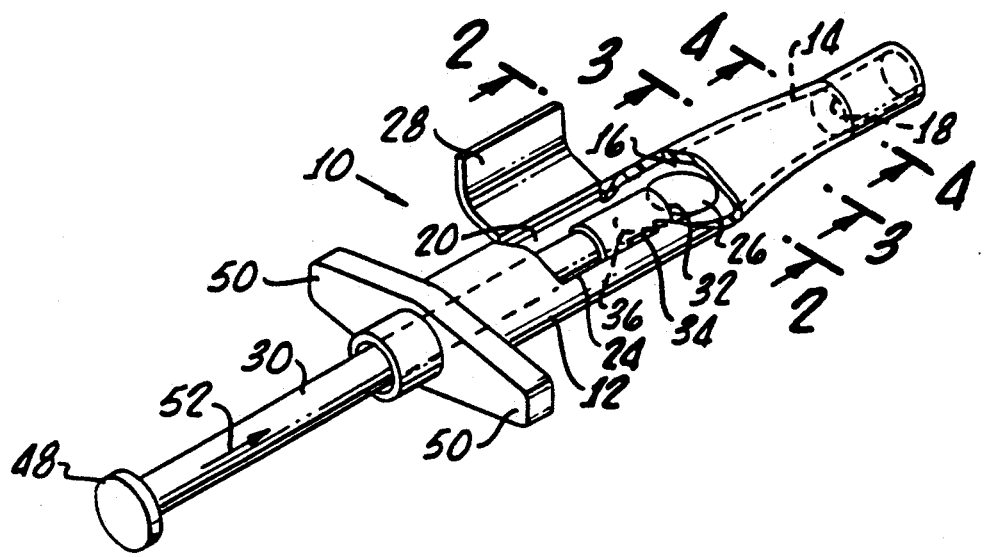
FIG. 1 is an isometric and partially cross-sectional view of an exemplary embodiment of the present invention illustrating the principles thereof.
Figure 1A:
FIGS. 1A and 1B are elevation views of typical intraocular lenses, 1A illustrating a peripheral flange haptic lens and 1B illustrating a lens with extending loop haptics.
Figure 1B:

A contoured-duct lens curling apparatus for both folding a flexible intraocular lens to reduce its effective size and for inserting the lens through a small ocular incision is shown in FIG. 1. An instrument 10 constructed in accordance with the teachings of the present invention includes a tubular body 12 provided with finger pull bars 50 adjacent to its proximal end, an intermediate portion interiorly defining a contoured duct 14, and a cannular portion 22 disposed at its distal end. The longitudinally disposed contoured duct 14 (shown in ghost lines), having an inlet 16 and an outlet 18, is in alignment with and communicating between a lens-receiving chamber 20 adjacent to the duct inlet and the cannula 22 adjacent to the duct outlet. A lens-admitting opening 24 in the periphery of chamber 20 provides access to chamber 20 for loading of a flexible intraocular lens 26 prior to curling and insertion of the lens. Lens 26 may be provided with either a peripheral flange 54 or extending loop haptics 36, 56, as more clearly illustrated in FIG. 1A showing the peripheral flange type of lens, and FIG. 1B showing the loop haptic type. Loading door 28 provides closure of the opening 24 against contamination and lens damage or loss after the lens is in place.

Body 12 also houses a plunger 30 disposed coaxially within body 12 and dimensioned to contact and displace lens 26 into duct 14 and through cannula 22. At its proximal end, plunger 30 has a thumbpiece 48. Finger pull bar 50, projecting at right angles to body 12, is mounted fixedly adjacent to the proximal end of the body 12 and is positioned to permit efficient displacement of coaxial plunger 30 by the thumb and fingers of a surgeon's hand in conjunction with thumbpiece 48. The distal tip 32 of plunger 30 is provided with a relief 34 configured to protectively accommodate a trailing haptic 36 of lens 26 as the lens is displaced from lens-receiving chamber 20 through contoured duct 14 and cannula 22 and finally through an ocular incision into the eye.

Figure 2:
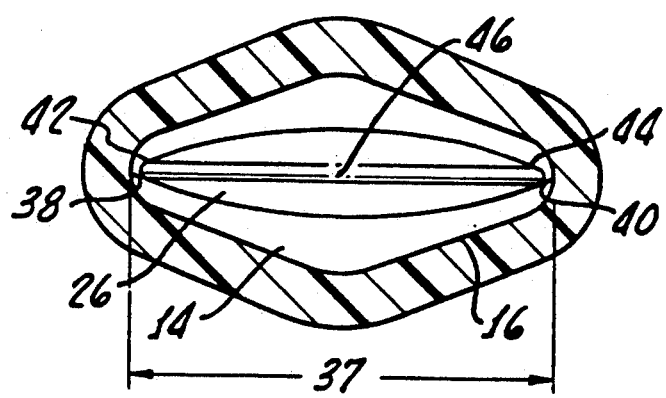
FIG. 2 is a sectional view taken along the plane 2—2 of the embodiment of FIG. 1 illustrating the placement of a flexible intraocular lens within the duct inlet.

As illustrated in FIG. 2, contoured duct inlet 16 is a generally rhombus-shaped aperture with its major axis 37 extending between the inlet ends of grooves 38 and 40, which are dimensioned to engage peripheral edges 42 and 44 of lens 26. As can be more clearly seen in FIG. 5, groove 38 extends longitudinally in an unbroken path from inlet 16 to outlet 18 of duct 14 to maintain the smooth lens-engaging and guiding groove 38 in continuous contact with lens peripheral edge 42. In like manner, groove 40 opposes groove 38 and engages lens peripheral edge 44, guiding it along the entire length of duct 14.

Figure 3:
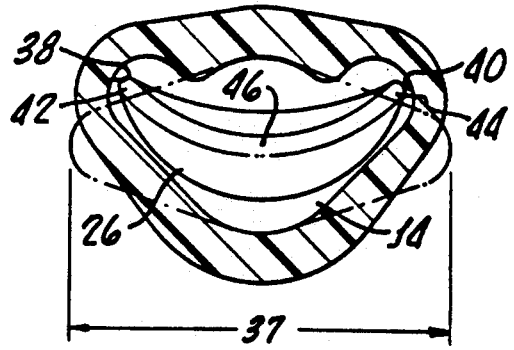
FIG. 3 is a sectional view taken along the plane 3—3 of the embodiment of FIG. 1 illustrating additional features of the present invention.

Referring now to FIG. 3, taken at 3—3 of FIG. 1, grooves 38, 40 are shown to have ascended from the lens initial plane that is determined by the intersecting of inlet major axis 37 with the longitudinal axis 46 of duct 14. Opposing edges 42, 44 of lens 26 are shown as they are guided upward equally about that diameter of lens 26 that is disposed longitudinally along duct axis 46 (shown in point perspective in FIG. 3).

Figure 4:
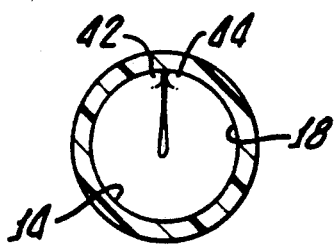
FIG. 4 is a sectional view of the embodiment of FIG. 1 taken along the plane 4—4 illustrating additional features of the present invention.

The cross-sectional form of lens 26 at outlet 18 is shown in FIG. 4, taken at 4—4 of FIG. 1, where duct 14 has attained the circular shape of outlet 18. Opposing lens edge portions 42 and 44 are shown in approximate contact with one another, thereby achieving a compact configuration of the lens that permits the lens to be inserted through an ocular incision on the order of one-half the unfolded diameter of the lens.

Figure 5:
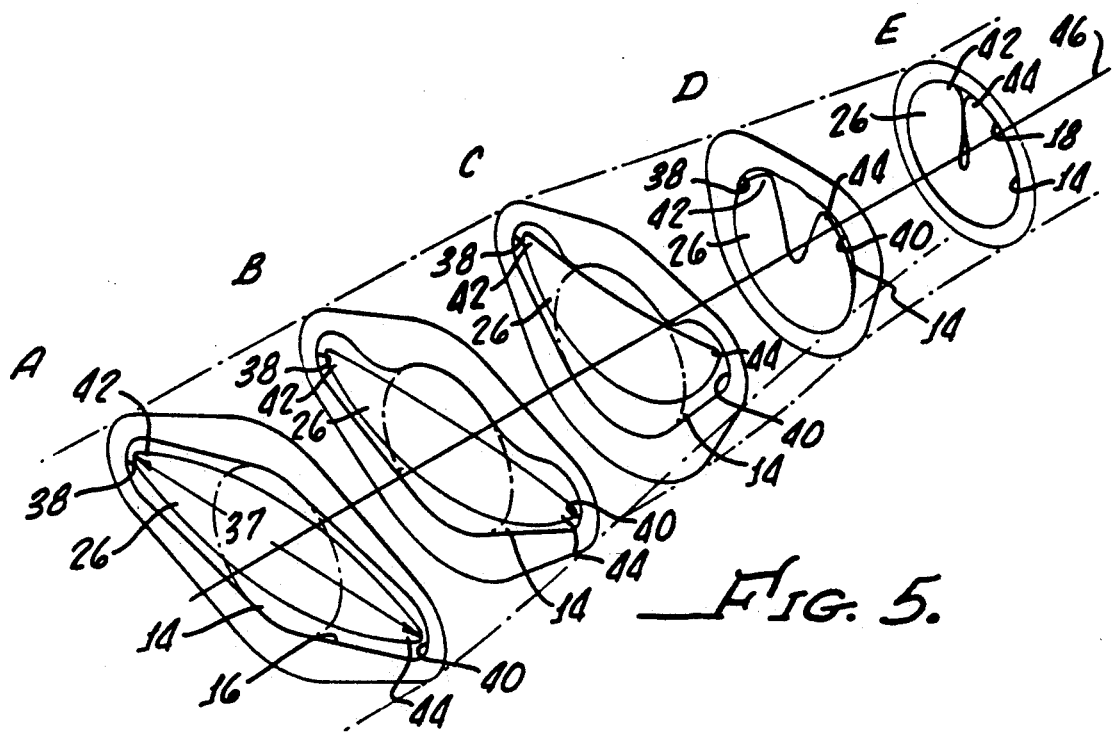
FIGS. 5 A-E are sequential phantom cross-sectional views of the apparatus embodying the present invention depicting an intraocular lens being advanced through the lens-curling duct thereof.

With reference to FIG. 5, the continuous changes in the interior contour of duct 14 are shown at representative cross-sectional positions 5A through 5E. Each position 5A through 5E illustrates the internal configuration of duct 14 at sequentially advanced locations within the duct. It will be readily understood that each cross-sectional view of lens 26 in FIG. 5 represents the same lens diameter within each position at a different stage of lens advancement and deformation.

For example, at the inlet position illustrated by FIG. 5A, corresponding with the sectional view of FIG. 2, lens 26 is shown in its relaxed state at the point it enters inlet aperture 16 where the inlet ends of grooves 38 and 40 accept lens edges 42 and 44 respectively. As the lens is advanced through duct 14, grooves 38, 40 begin to converge and rise from the initial plane defined by the intersecting of inlet major axis 37 with longitudinal axis 46 of duct 14. Although grooves 38 and 40 are converging and rising to guide the peripheral edges 42, 44 of lens 26, it will be noted that the cross-sectional area of the cylindrical path traversed by plunger 30, as defined by longitudinal axis 46, is sufficient to allow linear travel of plunger 30 as it advances lens 26 from inlet 16 through cannula 22. This cross-sectional area is shown by ghost circles congruently disposed in FIGS. 5A through 5C, with axis 46 describing the locus of the respective centers of the ghost circles.

FIG. 5C shows lens edges 42, 44 as they are guided toward each other within grooves 38, 40, with the form of lens 26 at this stage corresponding with that form illustrated in the sectional view of FIG. 3. Grooves 38, 40 are seen to be converging continuously from inlet 16 to outlet 18. At FIG. 5D, lens 26 has nearly completed its progression through the guiding grooves of duct 14, with the body of lens 26 continuing to fold along its longitudinally disposed diameter. Folding is complete at position 5E, showing lens edges 42, 44 brought substantially together at the outlet 18 of duct 14 as depicted in FIG. 4, with the lens prepared at this point for insertion as discussed below.

To implant a flexible intraocular lens in accordance with the teachings of the present invention, an ocular surgeon simply loads the lens 26 by introducing it into lens receiving chamber 20 through lens-admitting opening 24 so that the opposing peripheral edge portions 42, 44 of the lens are engaged within the grooves 38, 40 that form the sides of inlet aperture 16. Any trailing haptic 36 is then set within the relief 34 provided in tip 32 of plunger 30. After lens 26 is positioned within chamber 20 at inlet 16, loading door 28 is closed to prevent accidental loss of the lens or impairment of its biomedical suitability.

The surgeon then inserts cannula 22 into the small ocular incision (not shown) made for the lens implantation procedure. When the distal tip of cannula 22 reaches its desired location, the surgeon applies pressure to thumbpiece 48 with counterpressure provided by finger pull bar 50 to displace plunger 30 in the direction shown by the arrow 52 in FIG. 1. Tip 32 of plunger 30 exerts pressure to advance lens 26 through contact with the lens periphery, while plunger relief 34 prevents the haptic 36 whose loop lies between the plunger 30 and the lens 26 from the damage that could be caused by an unrelieved plunger tip.

Lens 26 is thus advanced steadily through contoured duct 14 and is simultaneously curled so that when lens 26 has reached the fully curled state shown in FIG. 4, and cannula 22 has been inserted into the ocular incision, plunger 30 continues to advance the lens through cannula 22 and into the intraocular region designated for implantation.

Figure 6:
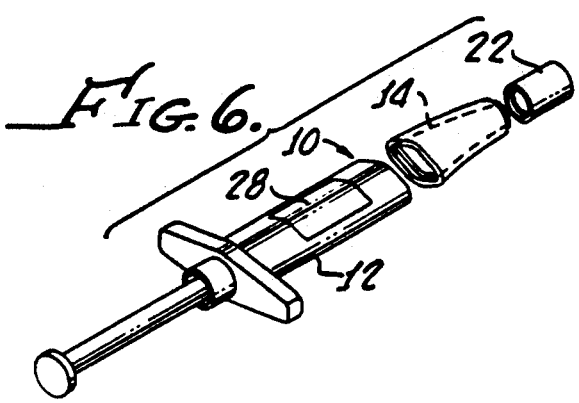
FIG. 6 is an exploded isometric view of an apparatus according to the present invention illustrating the detachability features of one embodiment thereof.

While an exemplary form of the invention has been shown in the drawings and described, variations in the exemplary form will be apparent to those skilled in the art. Main body 12, for example, may be made of a durable, easily machined material while contoured duct 14 may be a separate element detachably mounted as shown in FIG. 6 and independently fabricated. FIG. 6 also illustrates that cannula 22 may be detachable to facilitate sterilization and disposability. Additionally, the plunger 30 described as manually advanced may be replaced functionally by a another such element employing a different source of driving power. The invention therefore should not be construed as limited to the specific form shown and described, but instead is as set forth in the following claims.

We claim:

1. A contoured duct apparatus for curling and inserting a flexible intraocular lens into an eye with low radial pressure, said apparatus comprising:

a generally tubular body provided with a longitudinally disposed lens curling duct having a lens inlet end and an outlet end for insertion into an eye, said lens inlet end and outlet end connected by a pair of mutually opposing converging longitudinal lens-engaging grooves for guiding opposing edge portions of said lens toward one another with low radial pressure to a curled position as said lens is advanced through said duct from said inlet end to said outlet end; and means for advancing said lens through said duct from said inlet end through said outlet end.

2. The apparatus of claim 1 wherein said duct inlet end is an elongated transverse aperture having a major axis and wherein proximal ends of said lens engaging grooves are disposed at opposing ends of said major axis to slidingly engage diametrically opposed peripheral edge portions of said lens, said opposing longitudinal grooves converging from said inlet end to said outlet end toward one another and to a position above said major axis.

3. The apparatus of claim 1 wherein said outlet end is a generally circular transverse aperture.

4. The apparatus of claim 1 wherein said inlet end and said outlet end are coaxially aligned along a longitudinal axis of said duct.

5. The apparatus of claim 4 wherein said means for advancing is a coaxially aligned plunger longitudinally disposed within said tubular body and provided with a lens engaging tip.

6. The apparatus of claim 5 wherein said lens engaging tip is provided with a lens haptic receiving relief.

7. The apparatus of claim 1 further comprising a curled lens insertion cannula disposed in coaxial lens conducting communication with said outlet end.

8. The apparatus of claim 1 wherein said tubular body is provided with a lens receiving chamber disposed adjacent to said duct inlet end.

9. The apparatus of claim 8 wherein said lens-receiving chamber is provided with a peripheral lens admitting opening.

10. The apparatus of claim 9 wherein said lens admitting opening is provided with a loading door as a releasable closure.

11. An apparatus for inserting a flexible intraocular lens into an eye, said apparatus comprising:
a generally tubular body provided with a longitudinally disposed lens-curling duct having a longitudinal axis, an inlet end with a transverse major axis, and a generally circular outlet end longitudinally aligned with said inlet end, said duct having a pair of mutually opposed lens engaging grooves with proximal ends disposed at opposite ends of said major axis and dimensioned to engage and guide diametrically opposed peripheral edges of said lens, said pair of mutually opposed lens engaging and guiding grooves converging toward said outlet and terminating above the plane determined by the perpendicular intersecting of said inlet major axis with said duct longitudinal axis;
a lens receiving chamber disposed adjacent to said duct inlet and provided with a peripheral opening for access to the interior of said chamber;
a plunger longitudinally disposed within said tubular body and aligned coaxially with the longitudinal axis of said lens-curling duct; and
a cannula coaxially aligned with said duct at said duct outlet.

12. The apparatus of claim 11, wherein said lens receiving chamber peripheral opening is provided with a loading door.

13. The apparatus of claim 11, wherein said plunger is provided with a lens-engaging tip having a lens haptic receiving relief.

14. The apparatus of claim 11, wherein said lens-curling duct is detachably mounted to said tubular body adjacent to said lens-receiving chamber.

15. The apparatus of claim 11, wherein said cannula is detachably mounted to said lens-curling duct adjacent to said duct outlet.

16. A method for inserting a flexible intraocular lens into an eye with low radial pressure, said method comprising the steps of:
loading an uncurled lens into an apparatus having a lens-curling duct internally configured with converging grooves for guiding opposing peripheral edges of said lens toward one another with low radial pressure from a duct inlet to a duct outlet to form a curled reduced lens shape capable of passing through a minimal incision in the eye;
inserting said duct outlet into said incision; and
advancing said lens through the lens curling duct of the apparatus and out of the duct outlet into the eye.

17. The method of claim 16, wherein said loading step includes introducing said lens into a receiving chamber adjacent to said lens-curling duct.

18. The method of claim 17 wherein said advancing step includes displacing a plunger longitudinally along the interior of the apparatus from said receiving chamber through said lens-curling duct.

19. The method of claim 18 wherein said advancing step includes displacing said plunger through a cannular extension of said outlet.

20. The method of claim 16 wherein said inserting step comprises inserting a cannular extension of said outlet into said incision.

* * * * *